128-24 A AU 337 EX
6/23/87 XR 4,674,505

United States Patent [19]

Pauli et al.

[11] Patent Number: 4,674,505

[45] Date of Patent: Jun. 23, 1987

[54] APPARATUS FOR THE CONTACT-FREE DISINTEGRATION OF CALCULI

[75] Inventors: Karlheinz Pauli, Neunkirchen; Helmut Reichenberger, Eckental, both of Fed. Rep. of Germany

[73] Assignee: Siemens Aktiengesellschaft, Berlin and Munich, Fed. Rep. of Germany

[21] Appl. No.: 634,021

[22] Filed: Jul. 24, 1984

[30] Foreign Application Priority Data

Aug. 3, 1983 [DE] Fed. Rep. of Germany ....... 3328051

[51] Int. Cl.[4] .............................................. A61B 17/22

[52] U.S. Cl. .................................. 128/328; 128/24 A

[58] Field of Search .......................... 73/642; 310/335; 128/24 A, 328, 660, 804, 303.1; 350/474; 367/150

[56] References Cited

U.S. PATENT DOCUMENTS

| | | | |
|---|---|---|---|
| 3,168,659 | 2/1965 | Bayre | 73/642 |
| 3,245,251 | 4/1966 | Von Ardenne | 73/642 |
| 3,934,460 | 1/1976 | Sherwin | 73/642 |
| 3,942,531 | 3/1976 | Hoff | 128/328 |
| 3,958,559 | 5/1976 | Glenn | 310/335 |
| 3,982,223 | 9/1976 | Green | 367/150 |
| 4,001,766 | 1/1977 | Hurwitz | 73/642 |
| 4,131,025 | 12/1978 | Mezrich | 73/642 |
| 4,315,514 | 2/1982 | Drewes et al. | 128/24 A X |
| 4,333,347 | 6/1982 | Lang | 73/642 |
| 4,423,637 | 1/1984 | Soloway | 73/642 |

FOREIGN PATENT DOCUMENTS

| | | | |
|---|---|---|---|
| 2538960 | 4/1977 | Fed. Rep. of Germany | 128/24 A |
| 2902331 | 7/1980 | Fed. Rep. of Germany | 128/24 A |
| 2913251 | 10/1980 | Fed. Rep. of Germany | 128/24 A |
| 3119295 | 12/1982 | Fed. Rep. of Germany | 128/24 A |
| 53-87592 | 8/1978 | Japan | 128/328 |

OTHER PUBLICATIONS

Szilard, A New Ultrasonic Lens, Nov. 1976, pp. 268–272.

Rozhdestrenskaya, An Ultrasonic Focusing Transducer, Mar. 1979, pp. 261–263.

Chaussy, Extracorporeal Shock Wave, 1980, Berührungsfreie Nierensteinzertrümmerung durch extrakorporal erzengte, fokussierte.

Stasswellen, "Beiträge zur Urologie, vol. 2 (Karger, Basel, 1980), ISBN 3-8055-1901-X, Translation 1982, S. Karger AG, P.O. Box, CH-4009 Basel/Switzerland) ISBN 3-8055-3620-8.

Eisenmenger "Elektromagnetische Erzeugung Von Ebenen Druckstossen in Flusigkeiten" Akustische Beihefte, vol. 12 (1962) pp. 185–202.

*Primary Examiner*—Clifford D. Crowder

*Attorney, Agent, or Firm*—Hill, Van Santen, Steadman & Simpson

[57] ABSTRACT

The utilization of the apparatus fundamentally lies in the medical sector. An essentially planar shock wave is generated with the assistance of a shock wave tube via a magnetic dynamic effect. This shock wave is focussed by an acoustic convergent lens, whereby the calculus to be pulverized is placed at the focal point (F) of the convergent lens. In order to couple the shock wave to the patient, the space that the shock wave traverses is filled with a coupling agent, for example water. The shock wave tube, the convergent lens and a fine adjustment for the displacement of the convergent lens relative to the shock wave tube are attached to a mounting stand so as to be pivotable in all directions. This disintegration facility comprising a shock wave tube has high operating reliability with respect to high voltage, requires low maintenance, and has only negligible imaging or focussing errors resulting from the shock wave producing membrane and the convergent lens.

8 Claims, 2 Drawing Figures

APPARATUS FOR THE CONTACT-FREE DISINTEGRATION OF CALCULI

BACKGROUND OF THE INVENTION

The invention relates to a facility for the contact-free disintegration of a calculus located in the body of a living being and comprising a shock wave generator which can be directed to a target region in the body.

Facilities of this type are employed in medicine, for example for the pulverization of stones in the kidney of a human being. They are particularly advantageous because they avoid any and all surgical intervention in the body. It is not necessary to proceed surgically. The application of probes and devices to the calculus is likewise eliminated. A hazard due to infections or injuries, for example upon introduction of the probe or given surgical operations, cannot occur in the case of contact-free pulverization.

A facility of the type initially mentioned is disclosed in the German AS 23 51 247 (U.S. Pat. No. 3,942,531). Herein, a spark discharge is initiated between two electrodes at a first focus in a focussing chamber that is designed as a hemispherical ellipsoid of revolution. Said spark discharge causes a shock wave whose wave front propagates at all directions, i.e. spherically. The waves are reflected at the wall of the ellipsoid of revolution. They collect at the second focus of the elliptical reflector. The reflected waves arrive simultaneously at the second focus at which the calculus is located. The calculus is shattered under the focussed impact of the shock waves. The coupling between the one ellipsoid half and the body in which the calculus is located occurs via a thin film which presses against the body free of an air gap. The focussing chamber is filled with water.

This facility involves the disadvantage that changes in the shock wave energy are only possible within narrow limits and only with a considerable apparatus outlay by means of changing the spacing of the underwater electrodes. It is further disadvantageous that the mutual spacing of the electrodes must usually amount to a number of millimeters in order to generate high-intensity shock waves, the shock wave source therefore not having a punctiform geometry and imaging errors therefore possibly occurring in the focussing. Further, the underwater electrodes wear greatly with every discharge, so that their service life is limited, this requiring regular servicing of the facilities.

SUMMARY OF THE INVENTION

Given a facility of the type initially described, the object of the present invention is to increase the operating reliability, to obtain an imaging onto a target area with the smallest possible imaging error and to reduce maintenance requirements.

This object is inventively achieved in that a shock wave tube which is known per se (see Eisenmenger reference) and essentially generates a planar shock wave is provided as the shock wave generator; and in that a lens arrangement which focusses the shock wave onto a focal point in the target region is allocated to the shock wave tube.

Since this facility employs a shock wave generator which generates planar waves, only shock waves coming from one direction have to be collected and focussed. Imaging errors are thereby less probable than when spherical waves emanating from a spark gap region and proceeding in all directions must be focussed. The chronological and spatial reproducibility of the shock wave is significantly improved given generation thereof with a shock wave tube in comparison to generation with a spark gap. Maintenance work that arises due to wear and consumption of the electrodes of a spark gap is also eliminated. A shock wave tube generates the shock waves with the assistance of electromagnetic forces and does not require a spark gap.

A shock wave tube is constructed such that it contains a copper membrane at the one end of a fluid-filled, preferably water-filled tube, said copper membrane, separated by an insulating film, being disposed in front of a flat (or pancake) coil. The copper membrane is repelled from the flat coil on the basis of a current pulse therein and thereby generates the shock wave in the fluid. The copper membrane itself and the tube section adjacent thereto are usually placed at a common reference potential, i.e. they are grounded. High voltage is therefore not adjacent to the coupling agent which conducts the shock wave, the electrical safety of the patient and personnel being thereby increased.

Further advantages and details of the invention derive from the following description of an exemplary embodiment with reference to the accompanying sheet of drawings in conjunction with the claims; and other objects, features and advantages will be apparent from this detailed disclosure and from the appended claims.

DETAILED DESCRIPTION

Figure 1:
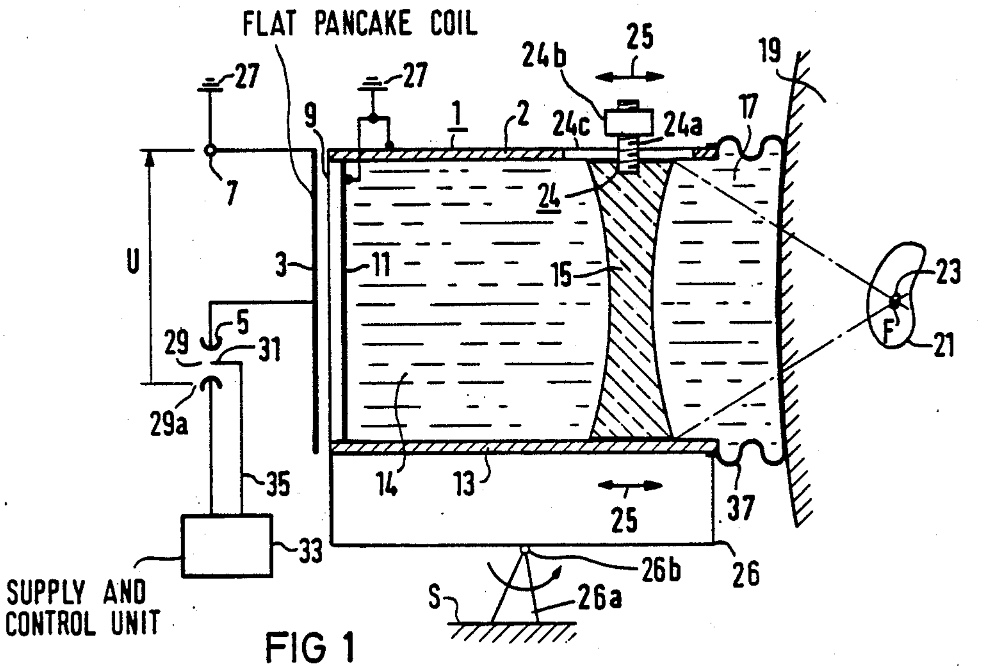
FIG. 1 shows a longitudinal section through a disintegration facility according to the invention, comprising a convergent lens.

In FIG. 1, a known shock wave tube 1 comprised of a jacket 2, of a flat (or pancake) coil 3 having two electrical terminals 5 and 7, of an insulating film 9, of a copper membrane 11 and of a metallic tube section 13 is placed in front of an acoustical convergent lens 15 which has a focal point F. The tuve section 13 is filled with a fluid 14, for example water.

The shock wave tube 1 is coupled to a body 19 via a coupling agent 17 having water-like acoustical properties. The body 19 of, for example, a patient has a calculus or concrement 23 in its kidney 21, e.g. a kidney stone.

The convergent lens 15 is displaceable relative to the jacket 2 of the shock wave tube 1 in opposite longitudinal directions as indicated by double arrows 25 via a fine adjustment means 24 comprising pin **24*a* and locking wheel 24*b*. the pin 24*a* is guided in a slot-shaped guideway 24*c* in the jacket 2 so as to provide for a range of adjustment corresponding to the longitudinal dimension of the slot forming guideway 24*c***.

The shock wave tube 1, the convergent lens 15 and the fine adjustment means 24 are mounted on a common stand, tripod or mounting plate. As shown in FIG. 1, a mounting plate 26 is attached to a support **26*a* so that plate 26 can be universally pivoted in all directions at a universal joing 26*b*, the support 26*a* also providing for adjustment of the plate 26 in all directions parallel to supporting surface S, as well as perpendicularly to this surface. As a result thereof, the shock wave tube 1 can be aligned with the calculus 23 such that the focal point F lies within the calculus 23**.

The copper membrane 11 and the tube section 13 are electrically connected to a safety potential such as ground 27, as is the terminal 7 of the flat coil 3. The other terminal 5 of the flat coil 3 is connected to a supply and control unit 33 via a switch 29 which includes an auxiliary contact 31.

A high voltage U is generated in the supply and contol unit 33 via a capacitor/resistor circuit (not shown). Said high voltage can amount to several kilovolts, for example 20 kV. The voltage U can thereby be varible. A control signal which is applied by the supply and control unit 33 to the auxiliary contact 31 via a control line 35 effects the closing of the switch 29 (to form an electrically conductive path between terminals 29*a* and 5). A part of the energy stored in the capacitor (not shown) of the supply and control unit 33 then discharges suddenly into the flat coil 3 which very quickly builds up a magnetic field. A current is induced in the copper membrane 11, said current being directed opposite the current in the flat coil and generating an opposing magnetic field. The copper membrane 11 is repelled from the flat coil 3 due to the dynamic effect of the opposing magnetic fields. This repulsion of the copper membrane 11 generates a planar shock wave, i.e. a sudden compression in the fluid 14 situated in front of the membrane 11. This shock wave has a steep rise in pressure, for example to 200 bar. The shock wave increases in steepness on its path through the tube section 13, the convergent lens 15 and the body 19 of the patient. In other words, the slewing rate or rate of raise of the shock wave increases on its path to the concrement 23. After passing through the convergent lens 15, the shock wave is directed such that it converges at the focal point F. The calculus 23 is placed there, and the focussed shock wave emits part of its energy content to the calculus 23 by means of tensile or compression forces, said calculus 23 being brittle in comparison to its enviroment. These forces decompose the calculus 23 into a number of parts and thus effect its disintegration.

This irradiation process must be repeated a number of times depending on the size and consistency of the calculus 23.

The shock wave tube 1 in the present embodiment has a diameter of approximately 100 mm and a length of approximately 150 mm. Also shorter shock wave tubes having a length of e.g. about 10 mm may be employed.

The disclosed disintegration facility offers the considerable advantage that the grounded copper membrane 11 and the grounded tube section 13 do not represent a source of hazard to the patient 19 or to the operating personnel. The electrical safety of the facility can even be increased for the operating personnel by means of an additional, insulating encapsulation (not shown), for example in the form of a synthetic coating of the outer surface of the jacket 2. Two-fold protection of the patient 19 against the electric high voltage derives given employment of a sack 37 filled with the coupling agent 17 at the place of entry of the shock wave into the patient 19. This protection is defined, on the one hand, by the insulating sack wall and, on the other hand, by the insulating film 9 in front of the flat coil 3.

The switch 29, moreover, can be integrated in the supply and control unit 33. It can also be placed at a distance from the shock wave tube arrangement. Since a spark gap need not be necessarily employed for the initiation, namely, vacuum switches or, more recently, SF-6 switches also, for example, come into consideration, the involved maintenance and service work that would be connected with the spark gap are eliminated.

Figure 2:
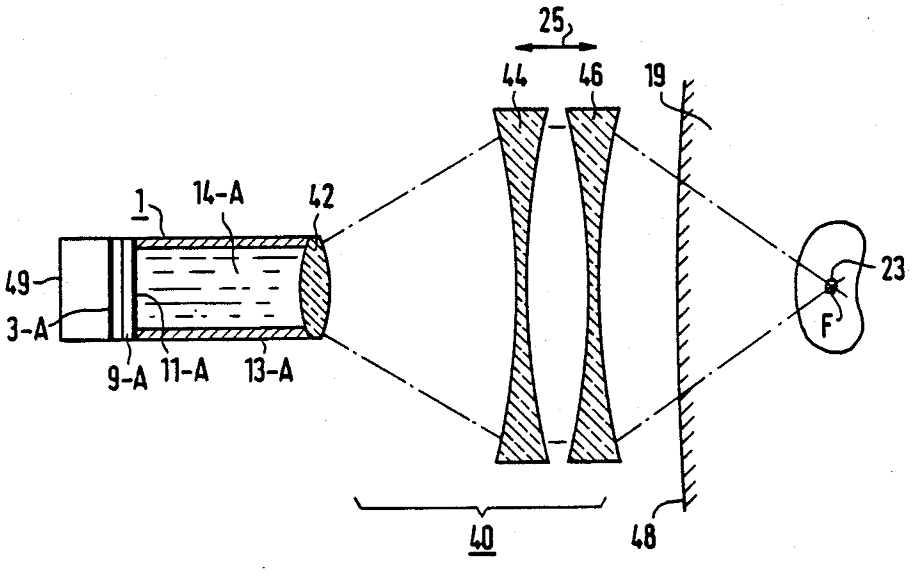
FIG. 2 shows a longitudinal section through a disintegration facility according to the invention, comprising a system of acoustic lenses.

FIG. 2 shows a known shock wave tube 1 to which a system 40 of acoustic lenses for imaging a planar shock wave onto a calculus 23 in the body of a patient 19 is allocated. The system 40 of acoustic lenses is comprised of a dispersing lens 42, of a condensor lens 44 and of a convergent lens 46 having a focal point F. The preferred material for the system 40 of acoustic lenses in plexiglass or polystyrene. The planar shock wave generated in the shock wave tube 1 is expanded in cross-section by the dispersing lens 42. The shock wave is aligned parallel by means of the condensor lens 44 and is focussed onto the focal point F by means of the convergent lens 46.

The developments of the shock wave tube 1 and of the holding means described to FIG. 1 also apply to this embodiment of the imaging system as shown in FIG. 2. Thus, the overall system of acoustic lenses here is displaceable relative to the shock wave tube 1 in an axial direction as indicated by the double arrow 25.

The advantage of this exemplary embodiment is that the shock wave enters into the body 19 of the patient over a larger cross-section of the body surface. As a result thereof, it is possible to keep the energy density in the tissue of the patient low, particularly at the body surface 48.

SUPPLEMENTARY DISCUSSION

In FIG. 2, the shock wave tube may comprise a carrier 49 for the spirally wound pancake coil 3-A. The electrical energizing system for coil 3-A may be the same as shown for the spirally wound coïl 3 in FIG. 1. Reference numeral 9-A in FIG. 2 may represent a disk-like insulating foil or film of minimum thickness so as to be comparable to the insulating layer 9 in FIG. 1. The flat coil 3, the insulating film 9 and the copper membrane 11 should be arranged close to each other in order to achieve a maximum emission effect. Similarly, the interface indicated in FIG. 1 between components 3 and 9, 13 merely for a clear illustration of the individual components should be avoided. The disk-like copper membrane 11-A in FIG. 2 may be grounded along with the cylindrical tube section 13-A. The parts 11-A, 13-A and 42 form a leak-tight chamber for receiving a fluid 14-A such as water. The jacket 13-A may be sealed to a wall of a water tank at an aperture in such wall using a flexible water proof coupling analogous to coupling 37, FIG. 1, so that the system 49, 3-A, 9-A, 11-A, 13-A, 42, 44 and 46 is universally pivotal relative to the water tank. In this case an open frame would connect parts 13-A, 42, 44 and 46 for joint horizontal displacement as represented by double arrow 25 as well as universal pivotal adjustment while the exterior of lens 42, and the lenses 44 and 46 remain immersed in the water tank along with body surface 48.

For the sake of a specific example, element 24*a*, FIG. 1, may be secured to the lens 15 and may be externally threaded so that nut element 24*b* with internal threads may be tightened thereon to clamp the lens 15 at a selected longitudinal position. Tube 13 may be cylindrical, and lens 15 may have mating cylindrical external surface fitting slidably within tube 13.

It will be apparent that many modifications and variations may be made without departing from the scope of the teachings and concepts of the present invention.

We claim as our invention:

1. An apparatus for the contact-free disintegration of a calculus located in the body of a living being, comprising:

a shock wave generator which can be aligned with a target region in said body, said shock wave generator comprising a shock wave tube means for generating a planar shock wave and which includes a metallic tubular jacket with a first and a second end;

at the first end of the tubular jacket a flat, spirally wound electrical coil, an insulating film and a conductive membrane being arranged in sandwich fashion, said flat coil having a first terminal for connection to a safety potential, and a second terminal for connection to a supply and control unit;

a lens means for focussing said planar shock wave onto a focal point in said target region, said lens means being operatively associated with said shock wave tube means and being arranged at the second end of said tubular jacket in spaced relationship to said conductive membrane;

a coupling fluid filling the space between said membrane and said lens means;

means for electrically connecting said conductive membrane and said jacket to a safety potential;

a coupling means provided between said lens means and said body for guiding the focussed shock wave to said body and for coupling said focussed shock wave therein;

alignment means for alignment of said shock wave tube means with said target region; and the shock wave tube means providing the planar shock wave with a sufficient intensity and the lens means sufficiently focusing it to permit disintegration of the calculus located in the body of the living being.

2. An apparatus according to claim 1 wherein the shock wave tube means has a diameter of approximately 100 mm.

3. An apparatus according to claim 1 wherein said alignment means comprises a find adjustment means for adjustment of a depth of said focal point in said body.

4. An apparatus according to claim 1 wherein said alignment means comprises a fine adjustment means for adjustment of said focal point perpendicularly to an emission direction of said focussed shock wave.

5. An apparatus according to claim 1 wherein said lens means is a single acoustic convergent lens.

6. An apparatus according to claim 1 wherein said lens means is a lens system comprised of a plurality of acoustic lenses.

7. An apparatus according to claim 6 wherein said lens system is comprised of an acoustic dispersing lens, of a condenser lens, and of an acoustic convergent lens.

8. An apparatus according to claim 1 wherein said lens means is displaceable relative to said tubular jacket in a longitudinal direction thereof.

* * * * *